US010736840B2

(12) United States Patent
Mistilis et al.

(10) Patent No.: US 10,736,840 B2
(45) Date of Patent: Aug. 11, 2020

(54) THERMALLY STABLE VACCINE FORMULATIONS AND MICRONEEDLES

(71) Applicant: Georgia Tech Research Corporation, Atlanta, GA (US)

(72) Inventors: Matthew Joseph Mistilis, Atlanta, GA (US); William Christopher Edens, Atlanta, GA (US); Andreas Sebastian Bommarius, Atlanta, GA (US); Mark Prausnitz, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 377 days.

(21) Appl. No.: 14/916,417

(22) PCT Filed: Sep. 3, 2014

(86) PCT No.: PCT/US2014/053902
§ 371 (c)(1),
(2) Date: Mar. 3, 2016

(87) PCT Pub. No.: WO2015/034924
PCT Pub. Date: Mar. 12, 2015

(65) Prior Publication Data
US 2016/0220483 A1 Aug. 4, 2016

Related U.S. Application Data

(60) Provisional application No. 61/873,032, filed on Sep. 3, 2013, provisional application No. 61/873,419, filed on Sep. 4, 2013.

(51) Int. Cl.
*A61K 9/00* (2006.01)
*A61K 39/165* (2006.01)
*C12N 7/00* (2006.01)
*A61K 39/12* (2006.01)
*A61K 39/145* (2006.01)
*A61K 39/00* (2006.01)

(52) U.S. Cl.
CPC ............ *A61K 9/0021* (2013.01); *A61K 39/12* (2013.01); *A61K 39/145* (2013.01); *A61K 39/165* (2013.01); *C12N 7/00* (2013.01); *A61K 2039/5256* (2013.01); *A61K 2039/70* (2013.01); *C12N 2760/16134* (2013.01); *C12N 2760/16234* (2013.01); *C12N 2760/16334* (2013.01); *C12N 2760/18434* (2013.01)

(58) Field of Classification Search
None
See application file for complete search history.

(56) References Cited

U.S. PATENT DOCUMENTS

| 6,887,484 | B2 * | 5/2005 | Bae ........................ A61K 39/29 424/184.1 |
| 6,960,193 | B2 | 11/2005 | Rosenberg |
| 7,211,062 | B2 | 5/2007 | Kwon |
| 7,488,801 | B2 | 2/2009 | Patten et al. |
| 8,062,573 | B2 | 11/2011 | Kwon |
| 8,216,588 | B2 | 7/2012 | Yamashita |
| 8,551,527 | B2 * | 10/2013 | Chouvenc ............ A61K 9/1623 424/193.1 |
| 8,784,843 | B2 | 7/2014 | Belin-Poput et al. |
| 8,865,182 | B2 | 10/2014 | Mayall et al. |
| 9,498,524 | B2 | 11/2016 | Ghartey-Tagoe et al. |
| 9,517,205 | B2 | 12/2016 | O'Hagan et al. |
| 9,687,536 | B2 | 6/2017 | Nagata et al. |
| 9,744,227 | B2 | 8/2017 | Bronshtein |
| 2002/0082543 | A1 | 6/2002 | Park et al. |
| 2002/0138049 | A1 | 9/2002 | Allen et al. |
| 2005/0137525 | A1 | 6/2005 | Wang et al. |
| 2005/0137531 | A1 | 6/2005 | Prausnitz et al. |
| 2008/0027384 | A1 | 1/2008 | Wang et al. |
| 2008/0213461 | A1 | 9/2008 | Gill et al. |
| 2008/0269666 | A1 | 10/2008 | Wang et al. |
| 2008/0286369 | A1 | 11/2008 | Moore et al. |
| 2009/0131905 | A1 | 5/2009 | Allen et al. |
| 2009/0182306 | A1 | 7/2009 | Lee et al. |

(Continued)

FOREIGN PATENT DOCUMENTS

EP 1954308 B1 9/2006
JP 2012090767 A 5/2012

(Continued)

OTHER PUBLICATIONS

Kommareddy et al. (Journal of Pharmaceutical Sciences, Mar. 2012, vol. 101, p. 1021-1027).*
Sullivan et al. (Nature Medicine, Jul. 2010, vol. 16, p. 915-921).*
Kim et al. (Advanced Drug Delivery Reviews, Nov. 2012, vol. 64, p. 1547-1568 in IDS on Apr. 7, 2016).*
Ferris (FluMist, Quadrivalent, Feb. 17, 2012, Department of Health and Human Services p. 1-60).*
Norman, James. J., et al., "Microneedle Patches: Usability and Acceptability for Self-Vaccination against Influenza", Vaccine, vol. 32, pp. 1856-1862, 2014.
Janeczko, Lorraine L., "Self-administered microneedle flu vaccine patches may be well accepted", Consultant, Mar. 7, 2014. [Retreived on Nov. 17, 2014]. Retrieved from the Internet: URL:www.consultant360.com/story/self-administered-microneedle-flue-vaccine-patches-may-be-well-accepted, 3 pages.

(Continued)

Primary Examiner — Agnieszka Boesen
(74) Attorney, Agent, or Firm — Eversheds Sutherland (US) LLP

(57) ABSTRACT

Formulations and methods are provided for stabilizing antigens in dry solid vaccines. One aspect relates to dry solid formulations of influenza vaccines including one or more excipients identified as imparting stability to influenza antigens. Another aspect relates to dry solid formulations of measles vaccines including one or more excipients identified as imparting stability to a measles antigen. The formulations may be in a form suitable for reconstitution in a physiologically acceptable liquid vehicle to form an injectable solution or suspension for administration to a patient or in the form of dissolvable microneedles or coated microneedles.

27 Claims, 13 Drawing Sheets

(56) References Cited

U.S. PATENT DOCUMENTS

| | | | |
|---|---|---|---|
| 2009/0232894 A1* | 9/2009 | Chouvenc | A61K 9/1623 424/489 |
| 2010/0074885 A1 | 3/2010 | Schiff et al. | |
| 2010/0312191 A1 | 12/2010 | Allen et al. | |
| 2011/0081380 A1 | 4/2011 | Francon et al. | |
| 2011/0112509 A1 | 5/2011 | Nozaki et al. | |
| 2011/0243988 A1* | 10/2011 | Ohtake | A61K 39/165 424/212.1 |
| 2012/0064126 A1* | 3/2012 | Sung | A61K 9/0075 424/400 |
| 2012/0123341 A1 | 5/2012 | Birchall et al. | |
| 2012/0220981 A1 | 8/2012 | Soo et al. | |
| 2013/0096532 A1 | 4/2013 | Ozel et al. | |
| 2013/0110078 A1 | 5/2013 | Moore et al. | |
| 2013/0129685 A1 | 5/2013 | Drew et al. | |
| 2013/0243841 A1 | 9/2013 | Kommareddy et al. | |
| 2013/0345638 A1 | 12/2013 | Heidenreich et al. | |
| 2014/0170299 A1 | 6/2014 | Gill et al. | |
| 2014/0276595 A1 | 9/2014 | Imran | |
| 2016/0120799 A1 | 5/2016 | Chiang et al. | |

FOREIGN PATENT DOCUMENTS

| | | |
|---|---|---|
| WO | 2011/156641 A2 | 12/2011 |
| WO | 2012/145739 A1 | 10/2012 |
| WO | 2013/082418 A1 | 6/2013 |
| WO | 2013/152092 A1 | 10/2013 |

OTHER PUBLICATIONS

U.S. Department of Health and Human Services, Centers for Disease Control and Prevention, "Report on the Global Immunization Division Research Program, 2011-2013", May 2014.

Kim, YC, et al. "Microneedles for Drug and Vaccine Delivery," Advanced Drug Delivery Reviews, vol. 64, No. 14, pp. 1547-1568, Nov. 2012.

Japanese Office Action dated Dec. 25, 2018 for JP Application No. 2016-540347 (9 pages with English translation).

Amorj et al., "Development of Stable lnfluenze Vaccine Powder Formulations: Challenges and Possibilities," Pharmaceutical Research, 2008,25(6):1256-1273.

Japanese Office Action dated Jun. 10, 2020 for JP Application No. 2016-540347 (11 pages with English translation).

Polley et al., "The use of beta-propiolactone for the preparation of virus vaccines," Canadian Jour. Microbiol. vol. 3, No. 6 (1957):863-870 (abstract).

* cited by examiner

THERMALLY STABLE VACCINE FORMULATIONS AND MICRONEEDLES

CROSS-REFERENCE TO RELATED APPLICATION

This application claims priority to U.S. Provisional Patent Application No. 61/873,419, filed Sep. 4, 2013, and U.S. Provisional Patent Application No. 61/873,032, filed Sep. 3, 2013, the disclosures of which are incorporated herein by reference.

STATEMENT REGARDING FEDERALLY SPONSORED RESEARCH OR DEVELOPMENT

This invention was made with government support under grant number EB012495 awarded by the National Institutes of Health. The government has certain rights in the invention.

BACKGROUND

The present application relates to formulations and methods for stabilizing viruses used in vaccines, particularly vaccines for influenza and measles. The application further relates to dry solid formulations of influenza and measles vaccines suitable for use in dissolvable microneedles or coated microneedles.

World Health Organization (WHO) statistics indicate that millions of people suffer from communicable diseases each year. For example, influenza is estimated to cause severe illness in 3 to 5 million people annually and results in as many as 250,000 to 500,000 deaths. Measles is estimated to infect more than 20 million people annually and results in over 150,000 deaths (mostly children under the age of five). The primary way to prevent these infections is successful vaccination campaigns.

For example, WHO estimates that interruption of measles transmission requires vaccine coverage rates in excess of 90%. This high bar requires a potent vaccine and a coordinated effort between vaccine manufacturers, public health experts, and health care personnel that administer the vaccines in the field. Thus, there are numerous obstacles that make the widespread dissemination of such vaccines more difficult.

Although a live measles vaccine has been available since the early 1960s, and is extremely effective when given correctly, storage requirements can impede its widespread dissemination as it is regarded as one of the more unstable live vaccines approved for human use. WHO estimates that more than 60% of the measles vaccine stock delivered into the field cannot be utilized due to spoilage, mishandling, or improper reconstitution.

Similar obstacles are faced with influenza vaccines, which currently are only available in liquid formulations that must be maintained at temperatures from 2-8° C. Thus, there is a need for dry solid formulations of vaccines that allow for the production of vaccines that have improved stability, are more easily transported, and are more convenient for mass vaccinations. Despite this need, development of dry vaccine formulations involves numerous variables that need to be considered. See e.g., Chen et al., "Opportunities and challenges of developing thermostable vaccines," Expert Rev. Vaccines 8(5), 547-557 (2009).

Some of the key considerations involved in preparing dry vaccine formulations include the exposure of virus to various thermal and mechanical stresses and the selection of excipients to minimize those damages. Furthermore, the formulation components must be compatible with the processing method chosen.

Freeze drying and spray drying are two of the widest used methods of drying active pharmaceutical ingredient (API) solutions in the pharmaceutical industry. Freeze drying has been employed to produce several commercial API products, including measles vaccines. The challenges of employing a freeze drying process on a labile biomolecule include the exposure of the virus to low temperature, adsorption of viral particles to ice crystal surface, and dehydration stress, to name a few.

Spray drying provides advantages of offering high volume product throughput (>5,000 lb/hr) and reduced manufacturing times over other protein preservation/drying technologies such as freeze drying. The challenge of using spray drying to stabilize thermally labile APIs, such as viruses, involves the control of three key areas: atomization conditions, drying conditions, and resultant solid state properties of the dried material. For example, during atomization, the process of breaking up the liquid stream into fine droplets can involve excessive shear stress, surface tension, and pressure applied to the product, leading to loss of bioactivity. Another challenge involves the control of droplet drying rate and its interplay with the components within each droplet. Depending on the process parameters, e.g., the drying rate and the droplet size, and the formulation components, e.g., surface activity and molecular size (i.e., diffusion rate), it is possible to manipulate the properties of the resultant dried particles, which include the particle size, surface composition, and surface morphology. This control is important, as the storage stability of the biopharmaceutical is generally influenced by the degree of its surface enrichment, as well as by the porosity and surface area of the spray dried particles. Numerous disadvantages are therefore associated with the most widely used methods of preparing vaccine formulations, including many disadvantages associated with the most commonly used dehydration techniques.

It therefore would be desirable to provide improved influenza vaccine formulations and improved measles vaccine formulations that are more stable and better suited for mass vaccination by providing simple, convenient, easy-to-administer dosage presentations. It also would be desirable to provide improved methods for preparing dry stable vaccine formulations.

SUMMARY

The present application addresses one or more of the foregoing desires and needs by providing dry solid formulations of influenza and measles vaccines having improved stability. Methods for their preparation are also provided, along with devices and methods for their administration to patients.

In one aspect, a vaccine composition is provided which includes an influenza antigen and an excipient selected from the group consisting of maltodextrin 17, maltodextrin 4, arginine, maltose, histidine, calcium heptagluconate, maltodextrin 13, heparin, raffinose, myo-inositol, sucrose, sorbitol, arabitol, fructose, potassium gluconate, adonitol, xylitol, sodium thiosulfate, asparigine, 2-hydroxypropyl-β-cyclodextrin, TRIS, sodium citrate, dulcitol, and combinations thereof.

In another aspect, a vaccine composition is provided including an influenza antigen and a blend of excipients selected from the group consisting of trehalose and arginine; trehalose and calcium heptagluconate; trehalose and matlodextrin 13; sucrose and arginine; arginine and calcium heptagluconate; arginine and maltodextrin 13; calcium heptagluconate and matlodextrin 13; maltodextrin 13 and sodium citrate; maltodextrin 13 and lactose; and sorbitol and sodium citrate.

In yet another aspect, a vaccine composition is provided including a measles antigen and an excipient selected from the group consisting of serine, sucrose, asparagine, glycine, threonine, histidine, trehalose, proline, sorbitol, maltose, taurine, dulcitol, and combinations thereof.

In another aspect, a vaccine composition includes a measles antigen, and a blend of excipients including an amino acid and a carbohydrate. The amino acid may be selected from the group consisting of serine, asparagine, glycine, threonine, histidine, proline, taurine, and combinations thereof. The carbohydrate may be selected from the group consisting of sucrose, trehalose, sorbitol, maltose, ducitol, and combinations thereof.

In still another aspect, a transdermal patch is provided including an array of microneedles which include one of the provided vaccine compositions.

In another aspect, methods of preparing vaccine compositions are provided including preparing an aqueous solution which includes either an influenza antigen or a measles antigen and one or more particular excipients or blends of excipients, and drying the solution at ambient temperature to form a dry solid vaccine composition.

In a further aspect, methods of vaccinating a patient are provided. In one embodiment, the method includes inserting one or more microneedles across the stratum corneum of the patient's skin, wherein the one or more microneedles include one of the provided vaccine compositions. In another embodiment, the method includes reconstituting one of the provided vaccine compositions in a physiologically acceptable liquid vehicle to form an injectable solution or suspension, and administering the injectable solution or suspension to the patient.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
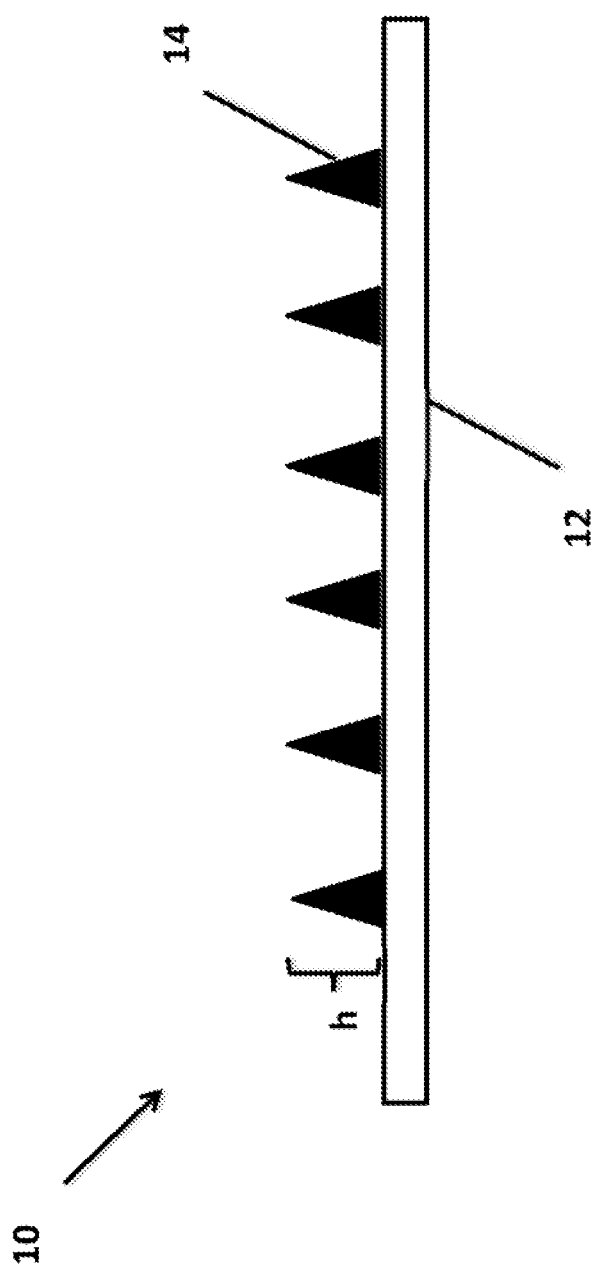
FIG. 1 is a side view of a plurality of microneedles comprising a vaccine composition according to an embodiment.
Figure 2:
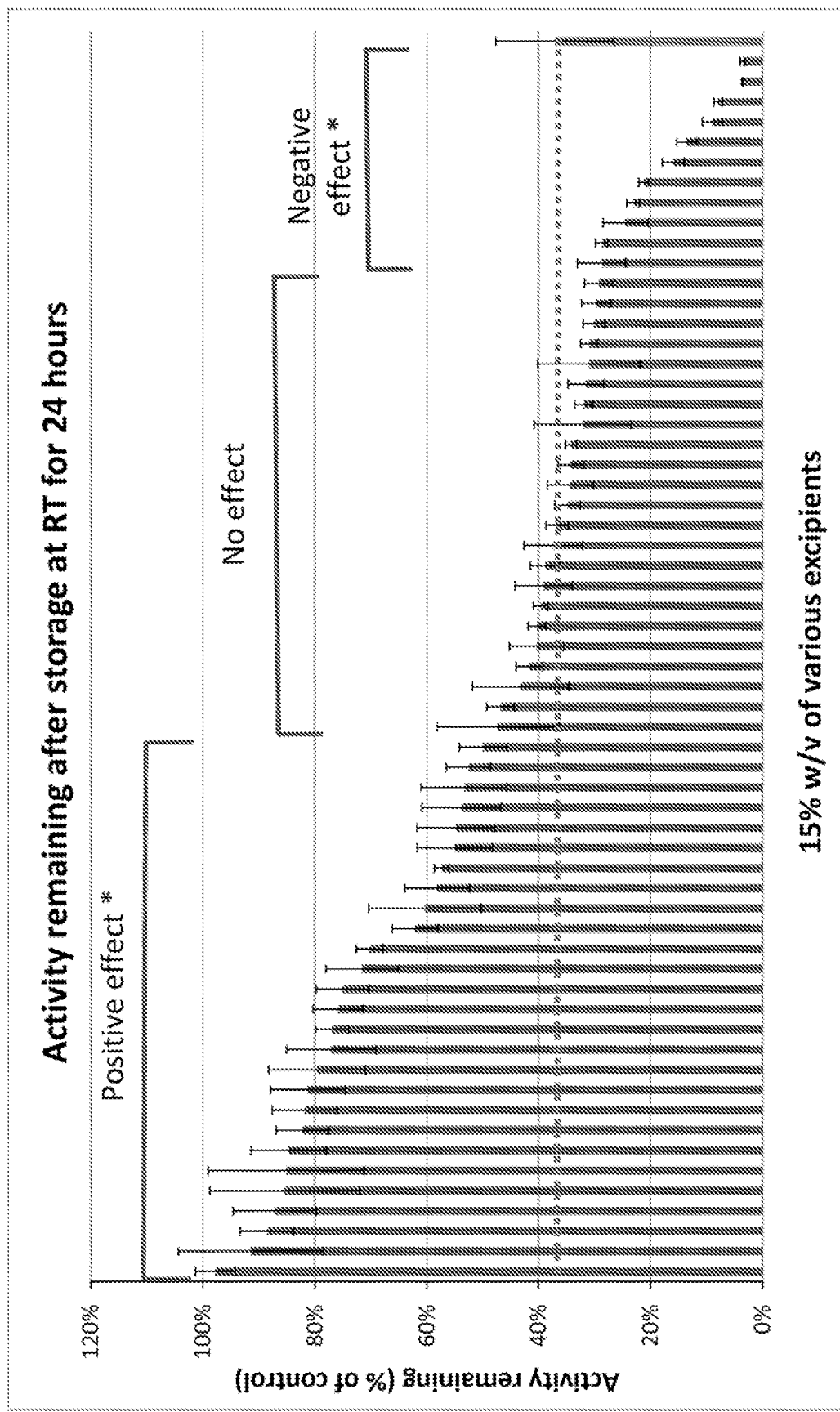
FIG. 2 is a bar graph showing relative haemagglutinin (HA) activity remaining after drying of various vaccine formulations.
Figure 3:
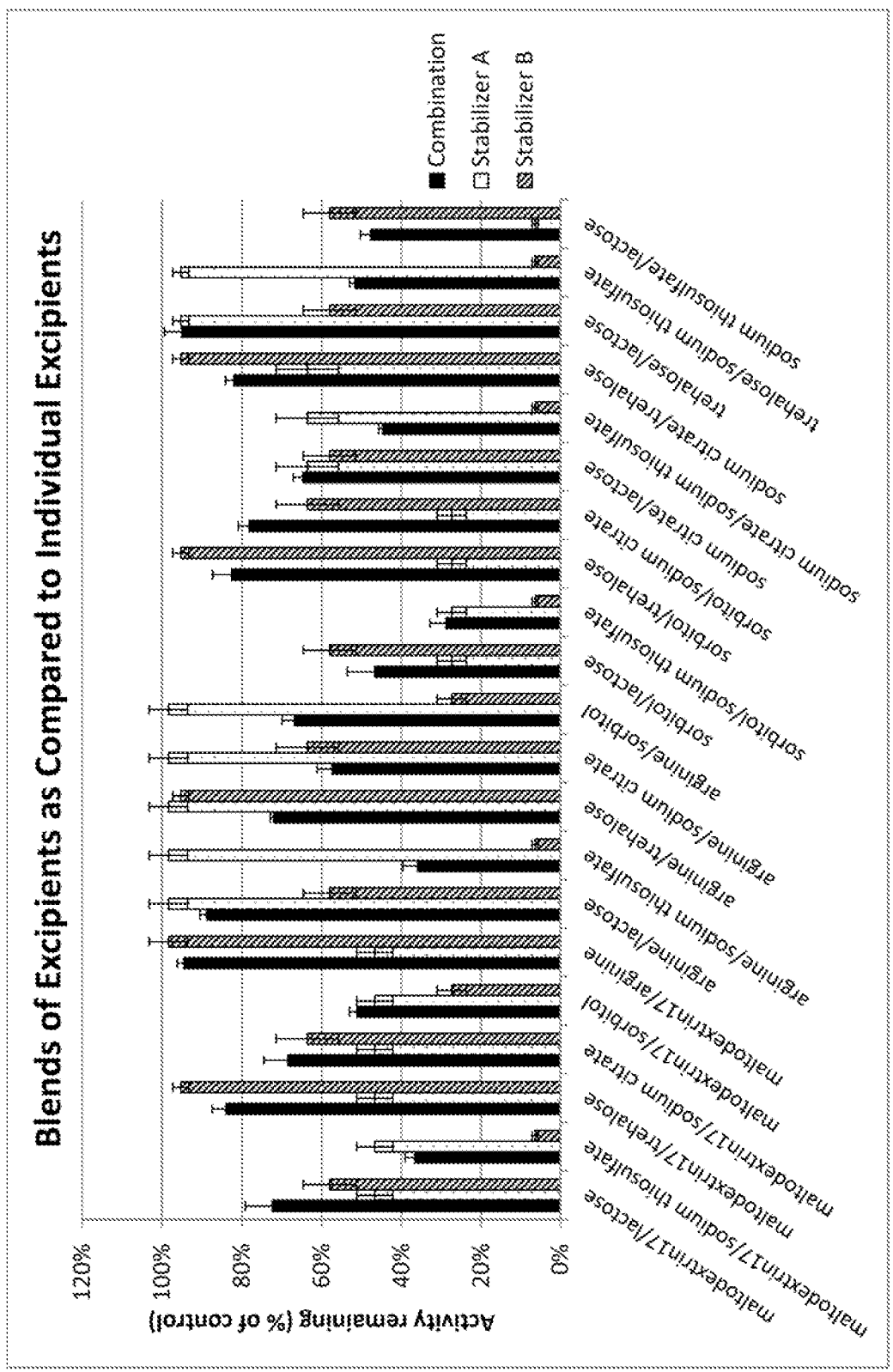
FIG. 3 is a bar graph showing relative HA activity remaining after drying of various blends of excipients as compared to the individual excipients.
Figure 4:
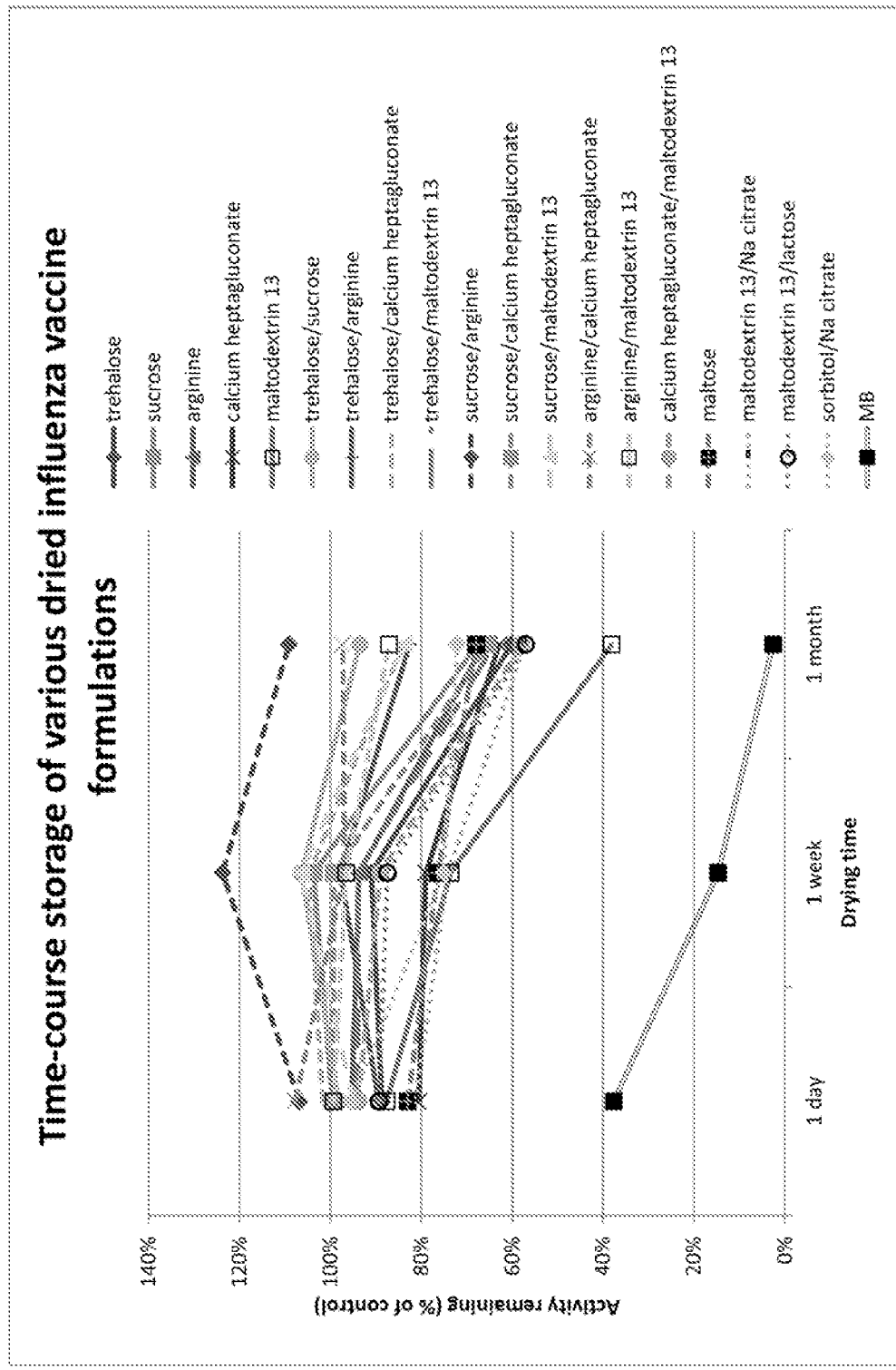
FIG. 4 is a line graph showing relative HA activity remaining after drying of various vaccine formulations after storage for various periods.

Dry solid forms of vaccine compositions for influenza or measles having improved stability have been developed. Screening processes were used to identify which excipients or excipient blends unexpectedly provided improved thermal stability to influenza or measles antigens from among the numerous excipients known in the art for use in pharmaceutical formulations. It has been discovered that by providing dry solid forms of the vaccine compositions comprising antigen combined with certain excipients, many of the problems commonly associated with loss of activity and spoilage of vaccines can be avoided, thereby decreasing wastage of the vaccine and increasing the amount of product available in vaccination campaigns or other vaccination scenarios.

Unless otherwise defined herein or below in the remainder of the specification, all technical and scientific terms used herein have meanings commonly understood by those of ordinary skill in the art to which the present invention belongs. It is also to be understood that the terminology used herein is for the purpose of describing particular embodiments only, and is not intended to be limiting. In describing and claiming the present invention, the following terminology will be used in accordance with the definitions set out below.

The term "about", as used herein, indicates the value of a given quantity can include quantities ranging within 10% of the stated value, or optionally within 5% of the value, or in some embodiments within 1% of the value.

As used herein, the term "ambient temperature" refers to typical controlled indoor temperatures, such as from about 16° C. to about 27° C., or more typically from about 18° C. to about 24° C., and often about 22° C.

A "stable" formulation or composition is one in which the biologically active material therein essentially retains its physical stability and/or chemical stability and/or biological activity upon storage. Stability can be measured at a selected temperature for a selected period. Trend analysis can be used to estimate an expected shelf life before a material has actually been in storage for that time period.

As used herein, the term "dry" or "dried" in reference to the solid vaccine formulations described herein refers to a composition from which a substantial portion of any water has been removed to produce a solid phase of the composition. The term does not require the complete absence of moisture. The vaccine compositions described herein generally have a moisture content from about 0.1% by weight and about 25% by weight.

Embodiments of the present application include vaccine compositions comprising one or more antigens and one or more selected excipients in a dry solid formulation. The one or more selected excipients have been discovered to advantageously improve the stability of the one or more antigens during drying and storage of the vaccine compositions.

In a preferred embodiment, the vaccine composition is in the form of a microneedle or a coating on a microneedle formed of another material. The vaccine composition becomes solubilized in vivo following insertion of the microneedle into a biological tissue, e.g., into the skin of a patient. Hence, the formulation microneedle or the formulation coating is referred to herein as being "dissolvable". In an alternative embodiment, the dry solid form of the vaccine formulation may be in a particulate or other form suitable for reconstitution before administration to a patient. For example, the vaccine composition may be reconstituted in a physiologically acceptable liquid to yield a solution or suspension suitable for injection via a hollow needle or hollow microneedle.

An exemplary microneedle array with a plurality of dissolvable microneedles is illustrated in FIG. 1. The microneedle array 10 includes a base substrate 12 with a plurality of microneedles 14. In embodiments, the plurality of microneedles 14 have a height from about 100 μm to about 2000 μm, from about 100 μm to about 1500 μm, from about 100 μm to about 1000 μm, or from about 500 μm to about 1000 μm. The array of the microneedles may have any suitable density. For example, the microneedles in the array may be arranged in even or staggered rows, wherein each microneedle is separated from its nearest neighboring microneedle by a distance about equal to the height of the microneedle. The array can include essentially any suitable number of microneedles. In one embodiment, the total mass of the vaccine composition in the microneedles of an array is suitable for delivering a prophylactically effective amount of the antigen to a patient. In non-limiting examples, the array may include from 5 to 10,000 microneedles, such as from 50 to 1000 microneedles or from 50 to 200 microneedles.

In some embodiments, the dissolvable microneedles may be formed by drying the vaccine composition in a suitable mold using methods described below. In other embodiments, the vaccine composition may be coated onto one or more microneedles comprising a biocompatible material, such as a metal, polymer, or silicon. Non-limiting examples of such microneedles and their methods of manufacture are disclosed in U.S. Pat. No. 6,334,856 and U.S. Patent Publication No. 2008/0213461.

The vaccine compositions may contain a biologically effective amount of the one or more antigens. As used herein, "biologically effective amount" refers to the amount of the one or more antigens needed to stimulate or initiate the desired immunologic response. Thus, the amount of the one or more antigens needed to achieve the desired immunological response will necessarily vary depending on a variety of factors including the type of antigen, the site of delivery (e.g., subcutaneous or intramuscular), and the dissolution and release kinetics for delivery of the antigen. For example, in embodiments it is desirable that the vaccine composition be formulated to dissolve in vivo over a period of dissolution from about 1 minute to about 60 minutes. As used herein, the "period of dissolution" or "dissolution period" means, in the case of dissolvable microneedles, the time it takes for the microneedle to be sufficiently wetted during administration such that the microneedle is substantially detached from the base substrate, or in the case of a coating on microneedles, the time it takes for the coating on the microneedle to be substantially detached from the microneedle during administration.

Influenza Vaccine Formulations

In embodiments, the antigen is an influenza antigen. The antigen may be prepared from influenza virions or expressed in a recombinant host and used in purified form. The antigen may take the form of a live virus or an inactivated virus, and may be a whole virus, split virus, subunit virus, or virus-like particle. For example, the influenza antigen may be a whole inactivated influenza virus, a split inactivated influenza virus, a subunit inactivated influenza virus, an influenza virus-like particle, or a combination thereof.

The influenza antigen may include one or more strains of the influenza virus, which are categorized as influenza A, influenza B, or influenza C. The compositions may include one antigen (monovalent), two antigens (2-valent), three antigens (trivalent/3-valent), or four or more antigens (4-valent or n-valent). For example, in embodiments the influenza antigen may be a combination of two influenza A strains and one influenza B strain or a combination of two influenza A strains and two influenza B strains. Non-limiting examples of influenza A strains include haemagglutinin (HA) subtypes H1, H2, H3, H4, H5, H6, H7, H8, H9, H10, H11, H12, H13, H14, H15, H16, H17, or H18, and neuraminidase (NA) subtypes N1, N2, N3, N4, N5, N6, N7, N8, or N9. Particular strains of the influenza antigen may include H1N1, H2N2, H3N2, H5N1, H5N3, H7N1, H7N7, H7N9, or H9N2.

The amount of the one or more influenza antigens in the vaccine formulation may be adjusted to obtain a desired immunologic response. In embodiments, a biologically effective amount an influenza antigen may be from about 1 μg to about 100 μg of HA per strain of influenza antigen. For example, a biologically effective amount of an influenza antigen in a dose-sparing influenza vaccine may be from about 1 μg to about 10 μg of HA per strain of influenza antigen; a biologically effective amount of an influenza antigen in a normal dose of seasonal influenza vaccine may be about 15 μg of HA per strain of influenza antigen; or a biologically effective amount of an influenza antigen in a high dose of seasonal influenza vaccine may be about 60 μg of HA per strain of influenza antigen. For example, the HA content of each strain in the trivalent vaccine typically is set at 15 μg for a single human dose, i.e., 45 μg total HA.

The influenza vaccine compositions further include one or more selected excipients found to increase the stability of the influenza antigen in a dry solid formulation as compared to a dry solid formulation of the influenza antigen without any excipients. In embodiments, the excipients that increase the stability of influenza antigens include maltodextrin 17, maltodextrin 4, arginine, treaholse, maltose, histidine, calcium heptagluconate, maltodextrin 13, heparin, raffinose, myo-inositol, sucrose, glucose, lactose, sorbitol, arabitol, fructose, potassium gluconate, cyclodextrin-γ, adonitol, xylitol, sodium thiosulfate, asparigine, 2-hydroxypropyl-β-cyclodextrin, TRIS, sodium citrate, and dulcitol. The excipient may be present in the vaccine composition in an amount from about 1% to about 90% by weight, from about 2% to about 75% by weight, from about 5% to about 50% by weight, or from about 5% to about 20% by weight.

In particular embodiments, the influenza vaccine compositions further include a selected blend of two or more excipients found to increase the stability of the influenza antigen in a dry solid formulation as compared to a dry solid formulation of the influenza antigen without any excipients. In particular embodiments, the blend of two or more excipients surprisingly provides a greater effect than that of any excipient alone, and in some cases provides a greater than additive effect of the multiple excipients on the stability of the influenza antigens. In embodiments, the blend of excipients that increase the stability of influenza antigens include trehalose and arginine; trehalose and calcium heptagluconate; trehalose and sucrose, trehalose and matlodextrin 13; sucrose and arginine; arginine and calcium heptagluconate; arginine and maltodextrin 13; calcium heptagluconate and matlodextrin 13; maltodextrin 13 and sodium citrate; maltodextrin 13 and lactose; and sorbitol and sodium citrate.

The blend of excipients may be present in the composition in a total amount from about 1% to about 90% by weight. For example, the blend of excipients may be present in the composition in a total amount from about 2% to about 75%, from about 5% to about 50%, or from about 5% to about 20%. The proportion of each excipient in the blend can be varied. In certain embodiments, the excipients in a blend of two excipients are present in the vaccine composition at a ratio from about 1:15 to about 15:1. For example, the excipients of the blend may be present in the composition at a ratio of about 1:9 to about 9:1, about 1:2, or about 1:1.

In embodiments, the vaccine composition further includes one or more adjuvants that increase the patient's immune response to the antigen. Suitable immune response augmenting adjuvants include, without limitation, aluminum gels or aluminum salts. For example, the adjuvant may be aluminum hydroxide, aluminum phosphate, or aluminum potassium sulfate. Additional adjuvants may include poly(I:C), imiquimod, and others known in the art.

The influenza vaccine compositions provided herein advantageously may be characterized as having improved stability. As used herein, "improved stability" of an influenza vaccine composition may be determined by using single-radial immunodiffusion (SRID) or an enzyme-linked immunosorbent assay (ELISA) to measure the HA activity of the composition when dissolved in an aqueous solution after storage for a given time and temperature. For example, the ELISA may be a typical sandwich ELISA in which a strain-specific antibody is coated onto a microwell plate and the aqueous solution of vaccine is incubated to allow the target antigen to bind to the immobilized antibody. Another strain-specific antibody which is conjugated with horse radish peroxidase (HRP) is then allowed to bind to the target antigen. Adding 3,3', 5,5'-Tetramethylbenzidine (TMB) to the microwells converts the HRP to a blue signal, which can be read and compared to a control.

For example, the vaccine composition may be characterized by an influenza antigen having improved stability in the composition over one month as compared to a comparative composition comprising the influenza antigen without an excipient, over three months as compared to such a comparative composition, over six months as compared to such a comparative composition, over nine months as compared to such a comparative composition, or over one year as compared to such a comparative composition.

In some embodiments, the stability of the composition is shown by the relative activity of the influenza antigen after storage at room temperature or at elevated temperatures of up to 40° C. as compared to the initial activity of the influenza antigen. For example, the stability of the composition may be characterized by the influenza antigen maintaining at least 50% of its activity after three months of storage at temperatures up to 40° C., at least 60% of its activity after three months of storage at temperatures up to 40° C., at least 70% of its activity after three months of storage at temperatures up to 40° C., at least 75% of its activity after three months of storage at temperatures up to 40° C., at least 80% of its activity after three months of storage at temperatures up to 40° C., or at least 90% of its activity after three months of storage at temperatures up to 40° C.

Measles Vaccine Formulations

In another aspect, the antigen is a measles antigen. Although the antigen may take the form of a live virus or an inactivated virus, the measles antigen is typically in the form of a live attenuated virus. In some embodiments, the measles antigen may be combined with a mumps antigen, rubella antigen, varicella antigen, or combinations thereof (each of which is most commonly in the form of a live attenuated virus).

The amount of the measles antigen in the vaccine composition may be adjusted to obtain a desired immunologic response. For example, the measles content in vaccines typically is set at 1000 $TCID_{50}$ to about 10,000 $TCID_{50}$ (where $TCID_{50}$ is defined as median tissue culture infective dose) for a single human dose. For example, a biologically effective amount of measles vaccine in the vaccine composition may be about 1,000 $TCID_{50}$.

The measles vaccine compositions further include one or more selected excipients found to increase the stability of the measles antigen in a dry solid formulation as compared to a dry solid formulation of the measles antigen without any excipients. In embodiments, the excipients that increase the stability of measles antigens include serine, sucrose, asparagine, glycine, threonine, histidine, trehalose, proline, sorbitol, maltose, taurine, dulcitol, and combinations thereof.

In particular embodiments, the measles vaccine compositions further include a selected blend of excipients including one or more amino acids and carbohydrates. In certain embodiments, the blend includes one or more amino acids selected from the group consisting of serine, asparagine, glycine, threonine, histidine, proline, taurine, and combinations thereof, and one or more carbohydrates selected from the group consisting of sucrose, trehalose, sorbitol, maltose, ducitol, and combinations thereof. In preferred embodiments, the amino acid comprises taurine or threonine, and the carbohydrate comprises sucrose, trehalose, or sorbitol. Other blends of excipients that are effective to stabilize the measles antigen include threonine and sucrose; threonine and trehalose; threonine and sorbitol; asparagine and trehalose; asparagine and sorbitol; serine and sucrose; serine and sorbitol; glycine and sucrose; glycine and trehalose; histidine and sucrose; taurine and sucrose; and taurine and trehalose.

The blend of excipients may be present in the measles vaccine composition in a total amount from about 1% to about 90% by weight. For example, the blend of excipients may be present in the composition in a total amount from about 2 to about 75%, from about 5% to about 50%, or from about 5% to about 20%. The proportion of each excipient in the blend can be varied. In certain embodiments, the excipients in a blend of two excipients are present in the vaccine composition at a ratio from about 1:15 to about 15:1. For example, the excipients of the blend may be present in the composition at a ratio of about 1:9 to about 9:1, about 1:2, or about 1:1.

The measles vaccine compositions provided herein advantageously may be characterized as having improved stability. As used herein, "improved stability" of a measles vaccine composition may be determined by using a tissue culture infective assay ($TCID_{50}$) after storage for a given time and temperature. Alternatively, improved stability may be determined using a genetically engineered measles variant that produces GFP upon replication as described in Example 8.

For example, the vaccine composition may be characterized by a measles antigen as having improved stability over one month in the composition as compared to a comparative composition comprising the measles antigen without an excipient, over three months as compared to such a comparative composition, over six months as compared to such a comparative composition, over nine months as compared to such a comparative composition, or over one year as compared to such a comparative composition.

In embodiments, the stability of the composition may be shown by the relative activity of the measles antigen after storage at room temperature or at elevated temperatures of up to 40° C. as compared to the initial activity of the measles antigen. For example, the stability of the composition may be characterized by the measles antigen maintaining at least 10% of its activity after one week of storage at temperatures up to 40° C., at least 10% of its activity after one month of storage at temperatures up to 40° C., at least 25% of its activity after one month of storage at temperatures up to 40° C., at least 50% of its activity after one month of storage at temperatures up to 40° C., at least 80% of its activity after one month of storage at temperatures up to 40° C., at least 10% of its activity after three months of storage at temperatures up to 40° C., at least 50% of its activity after three months of storage at temperatures up to 40° C., at least 80% of its activity after three months of storage at temperatures up to 40° C., at least 10% of its activity after six months of storage at temperatures up to 40° C., at least 50% of its activity after three months of storage at temperatures up to 40° C., or at least 80% of its activity after six months of storage at temperatures up to 40° C.

Methods of Manufacture

The influenza and measles vaccine formulations described herein generally are prepared by drying an aqueous solution comprising the antigen and selected excipient(s) on a suitable substrate. The aqueous solution may be prepared by mixing the one or more antigens and the one or more excipients in a solution comprising an aqueous buffer salt, non-limiting examples of which include HEPES, ammonium acetate, phosphate buffered saline, and potassium phosphate dibasic.

The aqueous solution may be dried on a variety of suitable substrates; however, it is preferred to that the substrate be selected to minimize loss of antigen activity during the drying process. For example, the aqueous solution may be dried on a metal substrate, a polymer substrate, a silicon substrate, or a textile substrate. In embodiments, the aqueous solution is dried on a polydimethylsiloxane (PDMS) substrate. In an embodiment, the substrate is a mold for forming one or more microneedles.

The aqueous solution may be dried at any suitable temperature and pressure conditions, which preferably are selected to maintain the biological activity of the antigen. In a preferred embodiment, the aqueous solution is dried at an ambient temperature for a time sufficient to form the dry solid form of the vaccine composition. For example, the aqueous solution may be dried at ambient temperature for a period from about 30 minutes to about one week to form the dry solid vaccine formulation (e.g., from about 45 minutes to about one week, from about one hour to about one week, from about one hour to about one day, etc.). In other embodiments, the aqueous solution may be vacuum-dried or dried using a combination of air-drying and vacuum-drying. Although various temperatures and humidity levels can be employed to dry the aqueous solution, the formulations preferably are dried at temperature from 1° C. to 60° C. (e.g., from 15° C. to about 45° C., from about 25° C. to about 45° C., or at about ambient temperature) and 0 to 10% relative humidity.

In one embodiment in which the vaccine composition is in the form of a dissolvable microneedle, the aqueous solution is poured into a mold for forming a microneedle or an array of microneedles prior to drying the solution. As used herein, "poured" or "pouring" the aqueous solution includes any suitable method for filling the mold with the aqueous solution, non-limiting examples of which include deposition, coating, printing, spraying, and microfilling techniques.

In embodiments in which the formulation is in the form of a coated microneedle, the microneedle or microneedle array is coated with the aqueous solution prior to drying the solution, for example, using the dip coating methods described in U.S. Patent Publication No. 2008/0213461.

After manufacture and prior to use, the vaccine compositions are packaged and stored under refrigeration, for example at temperatures from about 2° C. to about 8° C.; in a freezer, for example at temperatures below 0° C.; at ambient temperature; or at uncontrolled temperature, for example up to 50° C. The storage may be for the shelf life of the product or for a period less than the shelf life of the product. Vaccine vial monitors or other temperature indicators may be used to identify when the vaccine composition has exceeded a permissible level of thermal exposure. Advantageously, the vaccine compositions provided herein impart greater thermostability than previously existing formulations, thereby minimizing contamination, degradation, and loss of activity that can occur when the vaccine compositions are exposed to variable temperatures. Thus, the storage temperature for the vaccine compositions provided herein is less critical than for previously existing formulations.

Methods of Administration

The influenza and measles vaccine formulations provided herein may be administered to patients by any suitable means. As used herein, the term "patient" typically refers to a child or adult human in need of vaccination. Examples of suitable means of administration include injection and/or transdermal delivery via microneedle. For example, a patient may be vaccinated by inserting one or more microneedles, which are formed of or coated with the vaccine composition, across the stratum corneum of the patient's skin.

In another example, the vaccine composition is reconstituted in a physiologically acceptable liquid vehicle to form an injectable solution or suspension, and then the injectable solution or suspension is injected into the patient. The vaccine formulation may be reconstituted directly in a hypodermic syringe or in a sterile vial or other container. The reconstituted vaccine composition then may be injected into the patient, for example, by intramuscular, intradermal, or subcutaneous injection.

Embodiments of the present invention may be further understood with reference to the following non-limiting examples.

Example 1

Solutions of influenza vaccine were prepared using various surfactants to identify whether any negatively impacted the influenza antigen activity. The surfactants (Lutrol F68, Tween 20, SDS, CTAB, CHAPS) were added to the subunit influenza vaccine solutions (B/Brisbane/60/2008, 60 μg/mL HA) without other excipients, which were dried on stainless steel surfaces at ambient temperatures for 40 minutes. The vaccine was subsequently redissolved in a saline solution. This solution was evaluated with an enzyme-linked immunosorbent assay (ELISA) for measuring HA activity and compared to a stock of vaccine that had not been dried. When the effect of the surfactant on the control solution was accounted for, no significant difference was found between any of the surfactants tested on vaccine stability after drying (data not shown).

Example 2

Subunit influenza vaccine (B/Brisbane/60/2008, 60 μg/mL HA) was mixed with a variety of possible excipients at concentrations of 15% w/v in 150 mM ammonium acetate (Table 1). These solutions were dried on polydimethylsiloxane surfaces at ambient temperature and stored with desiccant for a total of 24 hours. The vaccine was then redissolved in a saline solution and assayed for activity as described in Example 1.

TABLE 1

| Tested Excipients | | |
|---|---|---|
| Maltodextrin 4 | Asparagine | Human Serum Albumin 1 (from blood with accompanying fatty acids and immonglobulins) |
| Arginine | 2-Hydroxypropyl-β-Cyclodextrin | Tryptophan |
| Trehalose | Tris(hydroxymethyl)-aminomethane (TRIS) | Tyrosine |
| Maltose | Sodium Citrate | Serine |
| Histidine | Dulcitol | Bovine Serum Albumin |
| Calcium Heptagluconate | Potassium Citrate | Creatine |
| Maltodextrin 13 | Ovalbumin | Leucine |
| Sucrose | Glycine | Potassium Sulfate |
| Glucose | Methyl Glucoside | Sodium Succinate |
| Heparin | Cyclodextrin-β | Isoleucine |
| Raffinose | Lysine | Ethyl Lactate |
| Myo-Inositol | Sodium Phosphate | Phenylalanine |
| Lactose | Valine | Arabinose |
| Sorbitol | Threonine | Potassium Phosphate |
| Arabitol | Galactose | Xylose |
| Fructose | Alanine | Potassium Sulfite |
| Cyclodextrin-γ | Methionine | Cysteine |
| Potassium Gluconate | Proline | Glycerol |

TABLE 1-continued

| Tested Excipients | | |
|---|---|---|
| Adonitol | Mannitol | Sodium Thioglycolate |
| Xylitol | Human Serum Albumin 2 (purified without fatty acids and immunoglobulins) | |
| Sodium Thiosulfate | Glutamine | |

The results are illustrated in FIG. 2 (p-values<0.05 when compared to unformulated vaccine). The bar on the right side of the figure represents vaccine with no added excipients. The excipients were generally categorized into 3 categories: excipients that showed a positive effect and imparted a stabilizing effect (maltodextrin 4, arginine, trehalose, maltose, histidine, calcium heptagluconate, maltodextrin 13, sucrose, glucose, heparin, raffinose, myo-insoitol, lactose, sorbitol, arabitol, fructose, cyclodextrin-γ, potassium gluconate, adonitol, xylitol, sodium thiosulfate, asparagine, 2-hydroxypropyl-β-cyclodextrin, TRIS, sodium citrate, and dulcitol), excipients that showed no statistically significant effect (potassium citrate, ovalbumin, glycine, methyl glucoside, cyclodextrin-3, lysine, sodium phosphate, valine, threonine, galactose, alanine, methionine, proline, mannitol, human serum albumin 2, glutamine, human serum albumin 1, tryptophan, tyrosine, serine, bovine serum albumin, creatine, leucine, and potassium sulfate), and excipients that further reduced the vaccine activity upon drying (sodium succinate, isoleucine, ethyl lactate, phenylalanine, arabinose, potassium phosphate, xylose, potassium sulfite, cysteine, glycerol, and sodium thioglycolate).

Example 3

Combinations of excipients were chosen to compare to stability provided by single constituent excipients. Subunit influenza vaccine (B/Brisbane/60/2008, 60 μg/mL HA) was formulated with one or two excipients at the same total excipient concentration (15% w/v), and then dried on polydimethylsiloxane surfaces at ambient temperature for one hour, and stored for 1 week at 40° C. with dessicant. The vaccine was redissolved in saline solution and then assayed for activity as described in Example 1. The results are illustrated in FIG. 3. Most combinations retained an amount of activity within the range of the constituent excipients; however, two combinations were shown to have superior activity as compared to their constituents—maltodextrin 17/lactose and sorbitol/sodium citrate.

Example 4

Formulations of subunit influenza vaccine (B/Brisbane/60/2008, 60 μg/mL HA) with various excipients (15% w/v) were dried on polydimethylsiloxane surfaces at ambient temperature for one hour, and stored with desiccant at 40° C. for up to one month. The vaccine was redissolved in saline solution and then assayed for activity as described in Example 1. The results are illustrated in FIG. 4.

Unformulated vaccine lost its activity very quickly. All other formulations performed well during short-term storage; however, only a few formulations had no statistically significant difference in activity over the entire study. These formulations included combinations of excipients, such as trehalose/sucrose, sucrose/arginine, and arginine/calcium heptagluconate.

Example 5

Figure 5:
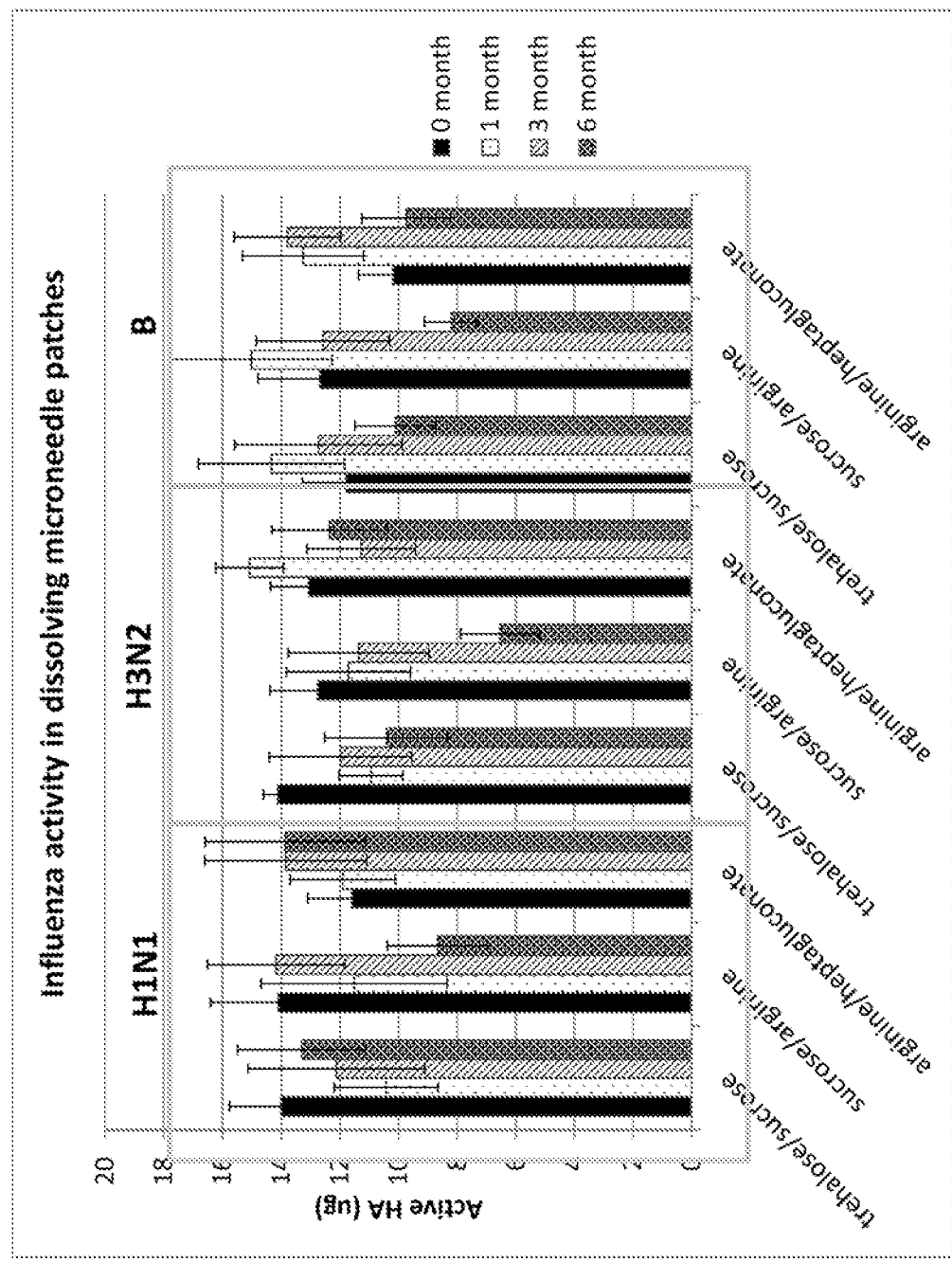
FIG. 5 is a bar graph showing the HA activity after drying of various trivalent subunit influenza vaccine formulations in microneedle patches and after storage for various periods.

Trivalent subunit influenza vaccine (B/Brisbane/60/2008, A/Brisbane/59/2007 (H1N1), and A/Victoria/210/2009 (H3N2), 1700-1850 µg/mL) was formulated with various combinations of excipients (total concentration of 15% w/v). Dissolving microneedle patches were produced with these formulations by drying the formulation in a polydimethylsiloxane mold at ambient temperature and under vacuum for 4 hours followed by additional drying in a desiccator at ambient temperature for 2 days, after which the microneedles were demolded, packaged in aluminum pouches with dessicant, and stored at 25° C. At given time points, some patches were dissolved in saline solution and assayed for activity of the three strains as described in Example 1. The results are illustrated in FIG. 5.

Example 6

Figure 6:
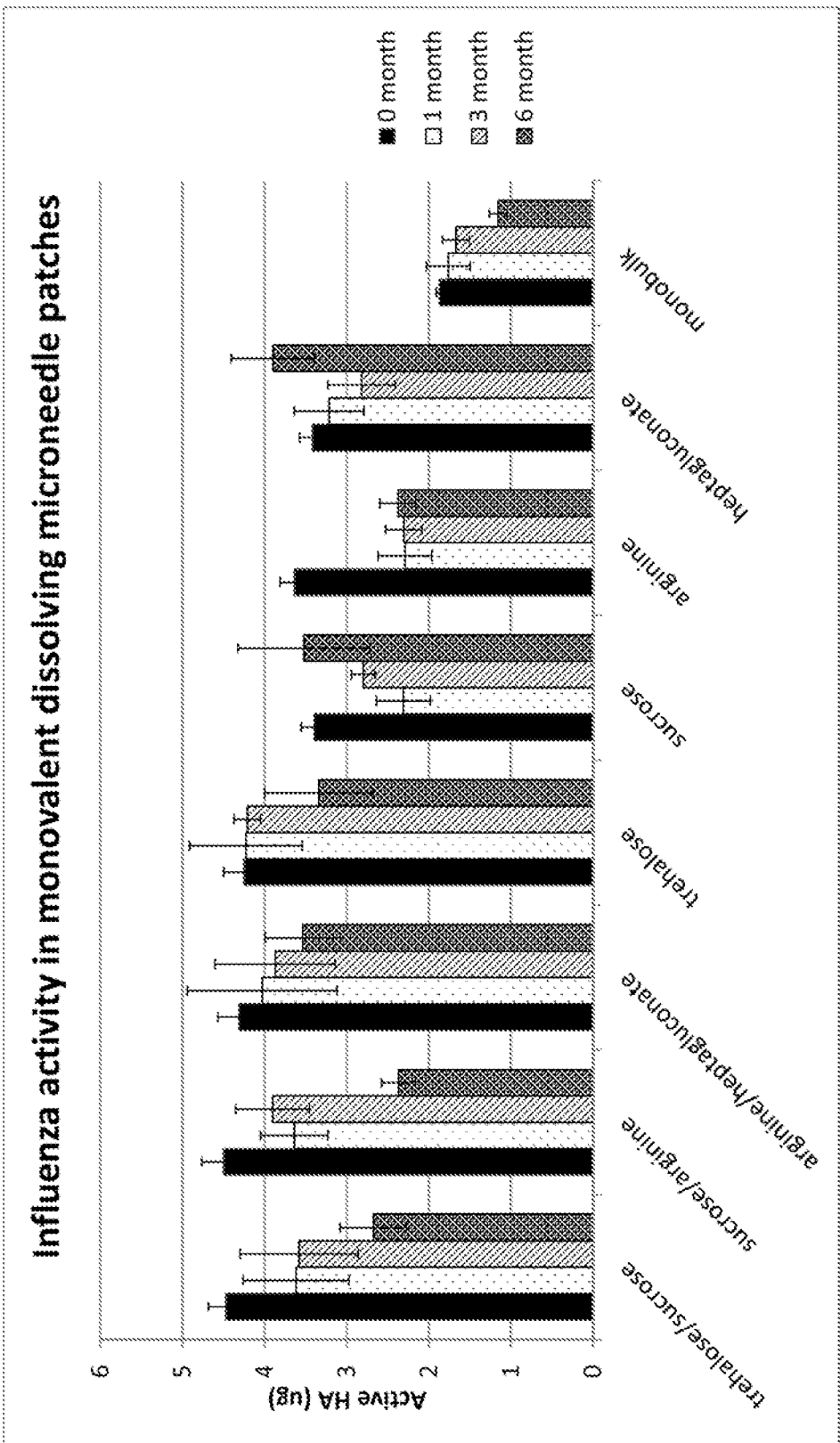
FIG. 6 is a bar graph showing the HA activity after drying of various monovalent subunit influenza vaccine formulations in microneedle patches and after storage for various periods.

Monovalent subunit influenza vaccine (B/Brisbane/60/2008, 630 µg/mL) was formulated with various excipients (10% w/v) or combinations of excipients (total concentration of 10% w/v in equal proportions). Dissolving microneedle patches were produced with these formulations as described in Example 5, and stored with desiccant at 25° C. At given time points, some patches were dissolved in saline solution and assayed for activity as described in Example 1. The results are illustrated in FIG. 6.

Example 7

Figure 7:
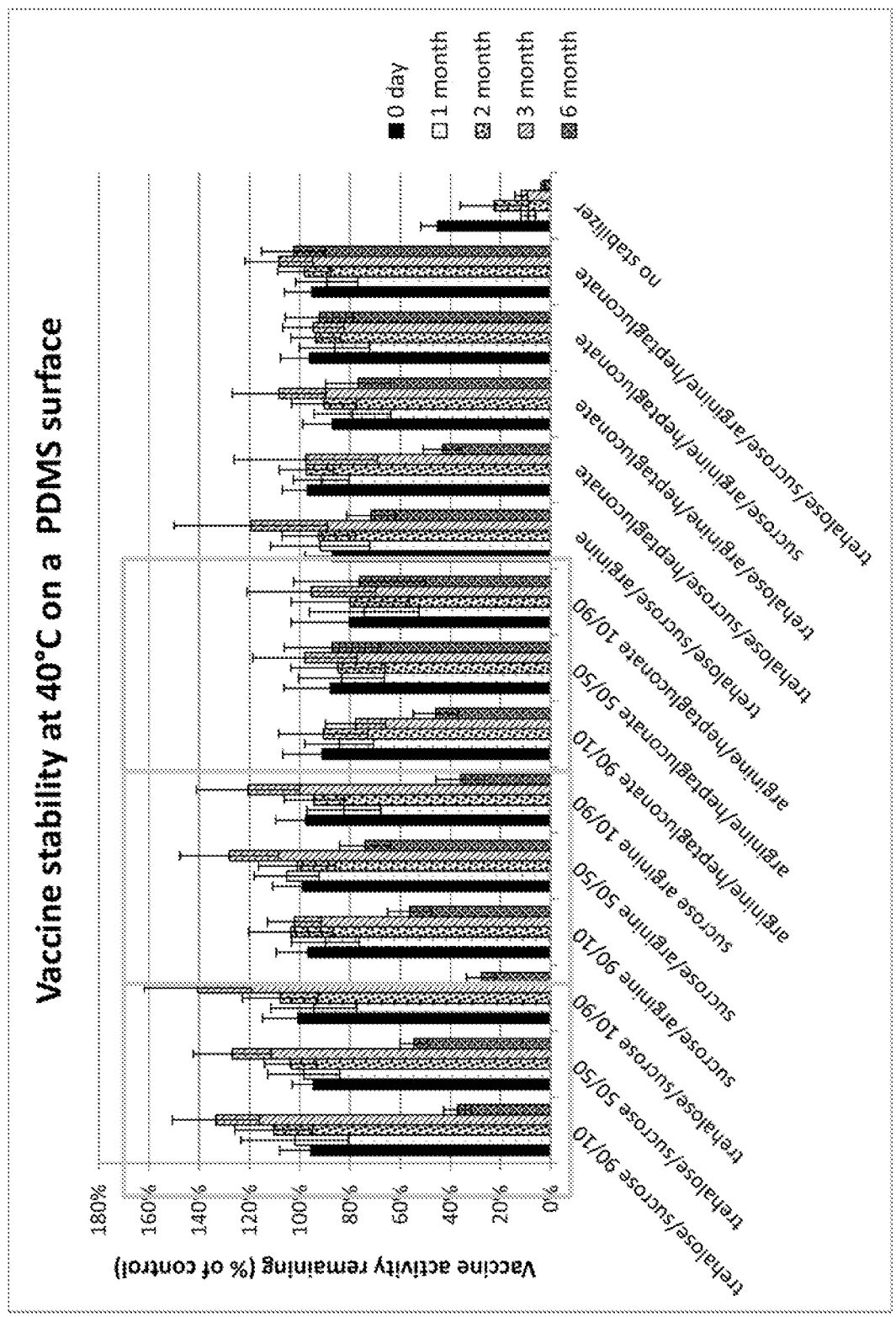
FIG. 7 is a bar graph showing the relative HA activity remaining after drying of monovalent subunit vaccine formulations in microneedle patches and after accelerated storage for various periods.

Subunit influenza vaccine (B/Brisbane/60/2008, 60 µg/mL) was formulated with excipients (10% w/v) or combinations of excipients (total concentration of 10% w/v in equal proportions). These formulations were then dried on polydimethylsiloxane surfaces at ambient temperature for one hour and stored at 40° C. with desiccant. At given times, the vaccine was redissolved in a saline solution and assayed for activity as described in Example 1. The results are illustrated in FIG. 7.

Example 8

A high-throughput assay was developed using eGFP-MeV in order to examine the stability of the measles virus after drying and storage at a range of temperatures. Genetically altered measles vaccine virus engineered to produce eGFP during replication was acquired from the lab of Dr. Paul DuPrex at Boston University. This stock was then propagated in Vero cells as previously described to increase the viral titer. The final titer was measured using a TCID50 assay to be $3.0 \times 10^5$ viral units/mL.

Various excipients were selected to evaluate stability of the altered measles virus. A list of excipients and the tested concentrations are provided in Table 2. All listed percentages represent a weight/volume percent of the aqueous solution prior to drying.

TABLE 2

| Tested Excipients & Concentration | |
| --- | --- |
| Alanine (300 mM) | Arabinose (15% w/v) |
| Arginine (300 mM) | Arabitol (300 mM) |
| Asparagine (300 mM) | Dulcitol (1% w/v) |
| Cysteine (300 mM) | Fructose (15% w/v) |
| Glutamine (300 mM) | Galactose (15% w/v) |
| Glycine (300 mM) | Lactose (5% w/v) |
| Histidine (300 mM) | Maltose (15% w/v) |
| Isoleucine (300 mM) | Raffinose (15% w/v) |
| Leucine (300 mM) | Sorbitol (15% w/v) |
| Lysine (300 mM) | Sucrose (15% w/v) |
| Methionine (300 mM) | Trehalose (15% w/v) |
| Phenylalanine (100 mM) | Xylitol (15% w/v) |
| Proline (300 mM) | Xylose (15% w/v) |
| Serine (300 mM) | Chitosan (5%) |
| Taurine (300 mM) | Human Serum Albumin (2%) |
| Threonine (300 mM) | Lactaalbumin Hydrosylate (2%) |
| Tyrosine (300 mM) | Magnesium Chloride (1M) |
| Valine (300 mM) | Magnesium Sulfate (1M) |
| | Sodium Oxalate (1%) |

All excipient formulations were mixed in a 1:1 ratio with a stock of eGFP-measles vaccine virus (eGFP-MeV) with a titer of $3.0 \times 10^5$ $TCID_{50}$/mL. A 3 µL sample of this formulation was then coated onto stainless steel chips that were placed into centrifuge tubes and stored in an opaque bag along with color-changing desiccant (Drierite, Sigma-Aldrich, St. Louis, Mo.) that was sealed to protect against moisture contamination. All samples were dried for 24 hours at 22° C. in a fume hood before storage for various periods of time. After removal from storage, the desiccant of each sample was checked for indication of moisture. If any contamination was detected the sample was discarded.

The dried samples were reconstituted with 1 mL of a solution of Dulbecco's Modified Eagle Medium (DMEM) (Gibco, Grand Island, N.Y.) containing 2% fetal bovine serum (FBS, Gibco) and tested for fluorescence activity using 96-well plates containing a monolayer of Vero cells. To each well in the plate, 100 µL of the reconstituted viral solution was added. The plates were incubated for 72 hours at 37° C. to encourage viral propagation. After incubation, each well was washed with 300 µL of sterile phosphate-buffered saline (PBS, Sigma-Aldrich) to remove media and uninfected viral particles. Any remaining solution was aspirated from the wells before testing. Detection of florescence was accomplished by measuring each well using a 96-well plate reader with an excitation wavelength of 485 and an emission wavelength of 520. The detected signal of each sample was compared to a positive control containing the same concentration of liquid eGFP-MeV.

Samples including the listed excipients were stored for a variety of times and temperatures to assess their ability to maintain the activity of eGF-MeV after drying. Excipients were eliminated from consideration in a step-wise fashion following exposure to more stringent conditions.

A stabilizing solution consisting of 300 mM of threonine (Sigma-Aldrich) and 15% w/v sucrose (Sigma-Aldrich) in DI-$H_2O$ was created for the final storage experiment. Samples were created using the method described above and stored at 4° C., 22° C. and 45° C. for between 1 and 24 weeks. A control consisting of a dried sample of eGFP-MeV containing no stabilizers stored at 22° C. for 1 to 4 weeks was also included.

All statistics were calculated using Prism software version 6.02 (Graphpad, La Jolla, Calif.). Comparisons between individual samples were done using an unpaired t-test was a significance cutoff of $p<0.05$. Comparisons between multiple samples were done using a two-way ANOVA with a Tukey post-test and a significance cutoff of $p<0.05$. The exponential best fit line was determined using Excel 2013 (Microsoft, Redmond, Wash.). Averages of all results represent the arithmetic mean of the tested samples.

Before proceeding to the stability screen, initial experiments were performed to better understand the parameters of the eGFP assay. Multiple 96-well plates containing confluent layers of Vero cells were infected with decreasing concentrations of eGFP-MeV and then allowed to incubate for 2, 3 or 4 days to examine how florescence activity changed over time. The results showed that after 3 days of incubation there was a linear correlation between viral concentration and fluorescence intensity starting at a concentration of 250 $TCID_{50}$/mL (not shown). This incubation time was chosen for all subsequent experiments.

Figure 8:
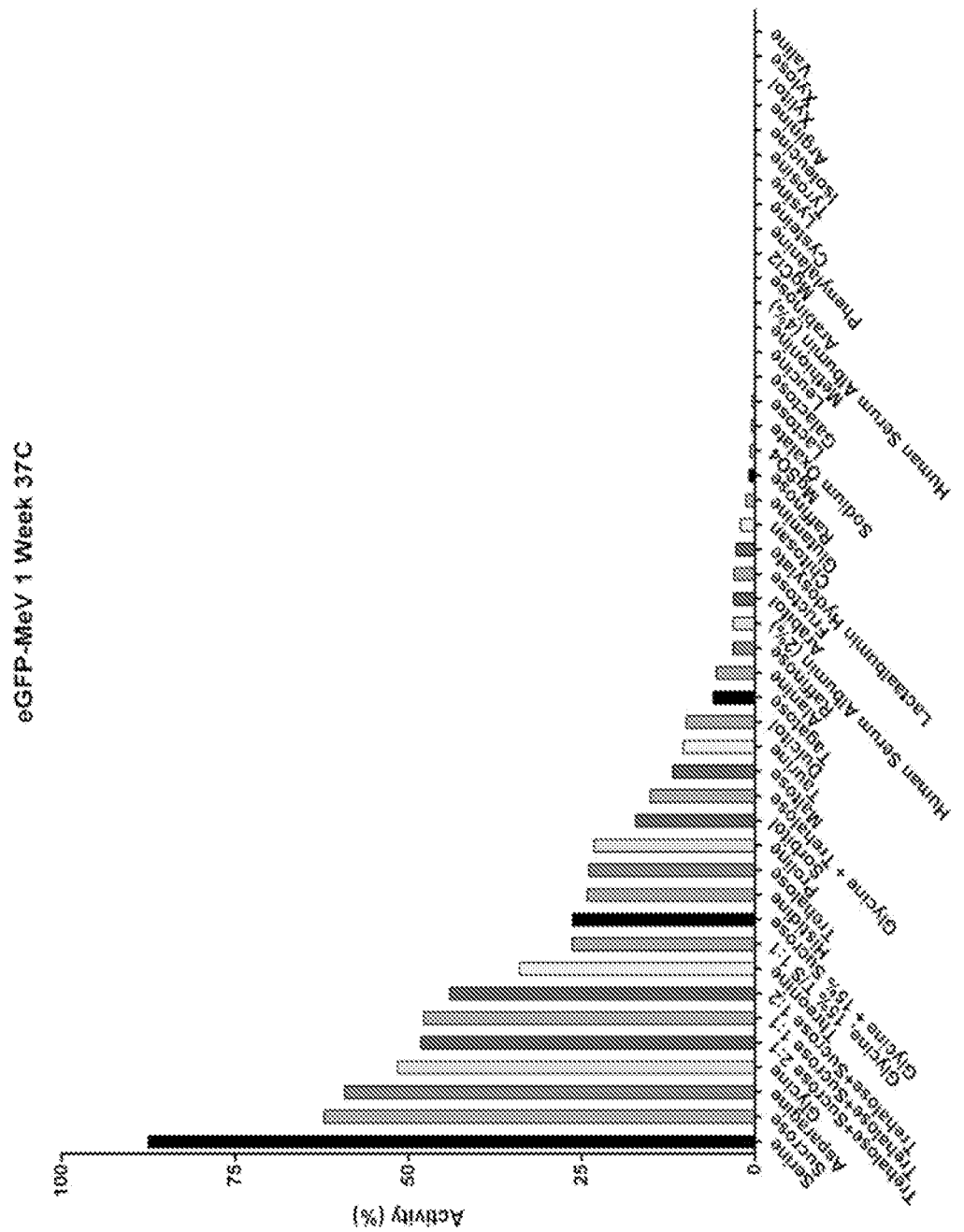
FIG. 8 is a bar graph showing the relative eGFP-MeV activity remaining after drying various measles vaccine formulations with various excipients and storage for one week at 37° C.

In order to rapidly assess the stabilizing potential of the initial list of excipients, a high temperature, short time storage study was performed. The initial screening study resulted in the elimination of the majority of the chosen excipients. After storage for 7 days at 37° C., approximately 41% of the tested samples retained less than 1% of their initial activity. The cutoff value of 10% remaining activity was chosen because it corresponds to the WHO requirement for live-attenuated measles vaccine stored for 1 week at 37° C. This resulted in the elimination of about 60% of the initial list (FIG. 8). After the initial screen, 14 samples were chosen for further investigation in the second screening experiment.

Figure 9:
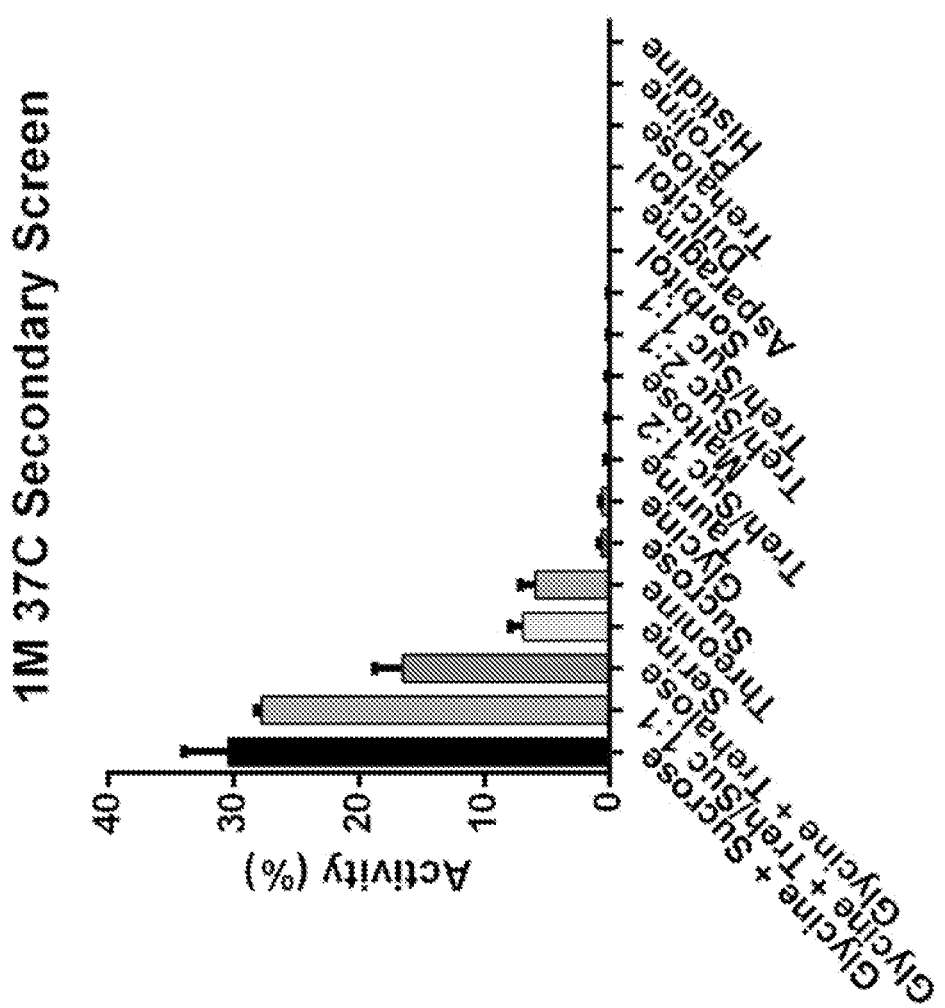
FIG. 9 is a bar graph showing the relative eGFP-MeV activity remaining after drying various measles vaccine formulations with various excipients and storage for one month at 37° C.

In order to further assess the stabilizing potential of the remaining excipients, a longer storage condition was chosen for the second screen. After 1 month at 37° C., only 4 samples demonstrated remaining activity of more than 1% (FIG. 9). During this secondary screen, it was noticed that when the excipients glycine and sucrose individually exhibited extremely low stabilizing activity (0.53% and 0.61% activity remaining respectively); however, when these excipients were combined, the remaining activity of the dried vaccine increased significantly to 30.45% (p<0.0005). This led to investigation of the effect of using a larger range of carbohydrate sugar and amino acids to stabilize the measles vaccine.

Figure 10:
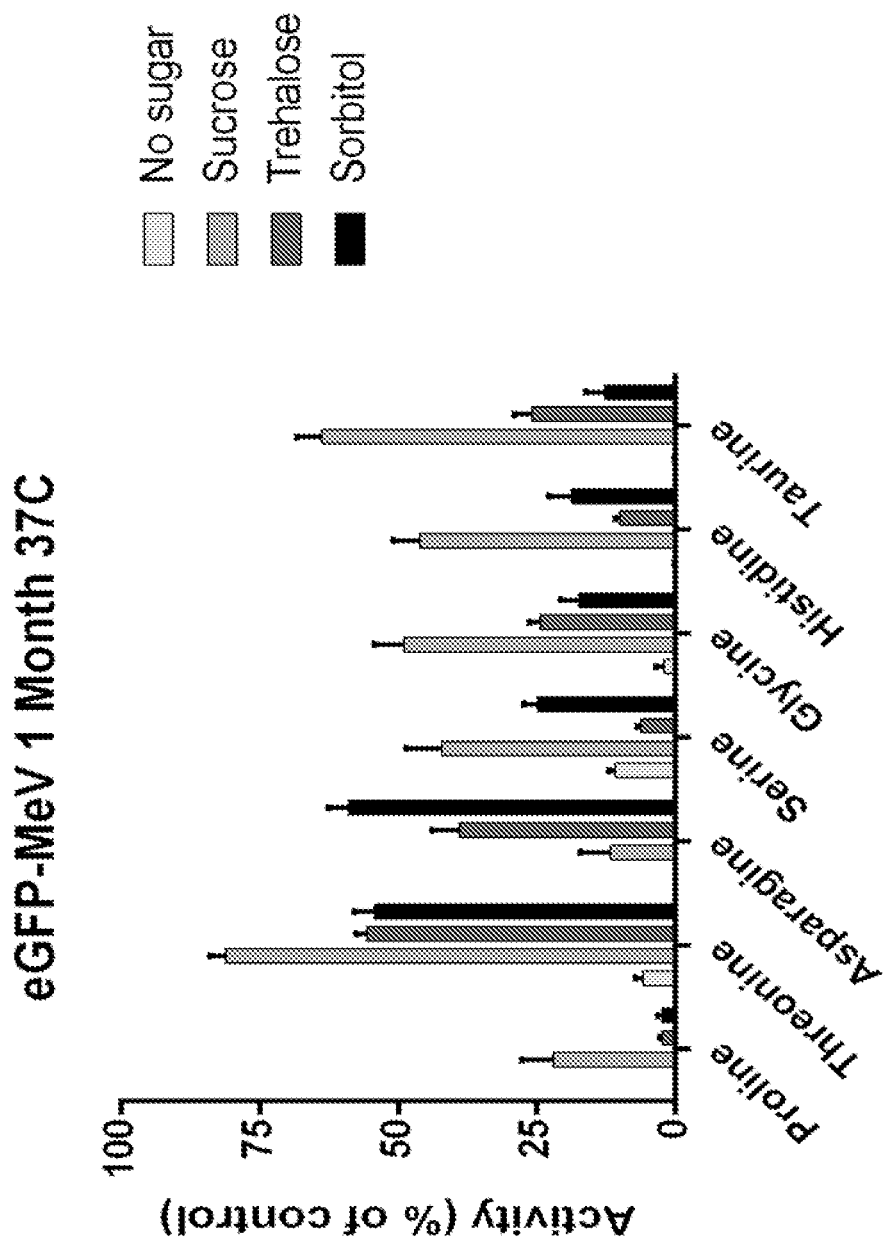
FIG. 10 is a bar graph showing the relative eGFP-MeV activity remaining after drying various vaccine formulations with blends of excipients and storage for one month at 37° C.

Combinations were made of all excipients in these two categories that exhibited any stabilizing activity during the initial screen. All of the amino acids were also tested individually to serve as a control. After storage for 1 month at 37° C. the results matched the earlier observations, with every amino acid tested exhibiting a higher stabilizing ability when paired with a carbohydrate sugar (FIG. 10). Sucrose was determined to be the most potent secondary stabilizer, as combinations including sucrose had the highest remaining activity for 6 of the 7 tested amino acids. A cutoff limit of 40% was used for this screen to exclude stabilizing combinations which had lower activity.

Figure 11:
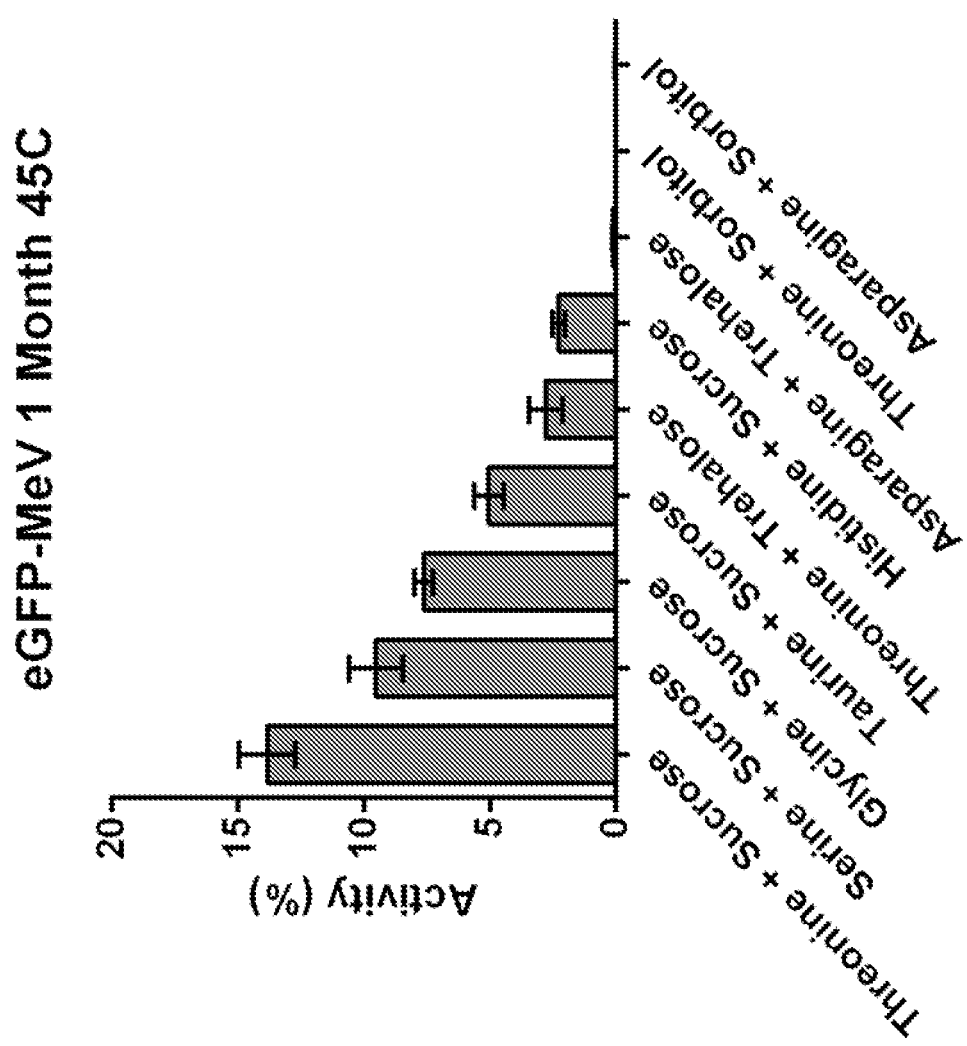
FIG. 11 is a bar graph showing the relative eGFP-MeV activity remaining after drying various vaccine formulations with blends of excipients and storage for one month at 45° C.

A final screen was carried out to determine the best combination of excipients to use for more extensive stability experiments. After storage for 1 month at 45° C., the remaining activity of each sample was tested. This screen showed that a combination of the amino acid threonine and the sugar sucrose had the highest stabilizing potential (FIG. 11), retaining nearly 14% of its original activity after storage at this harsh temperature condition.

Figure 12:
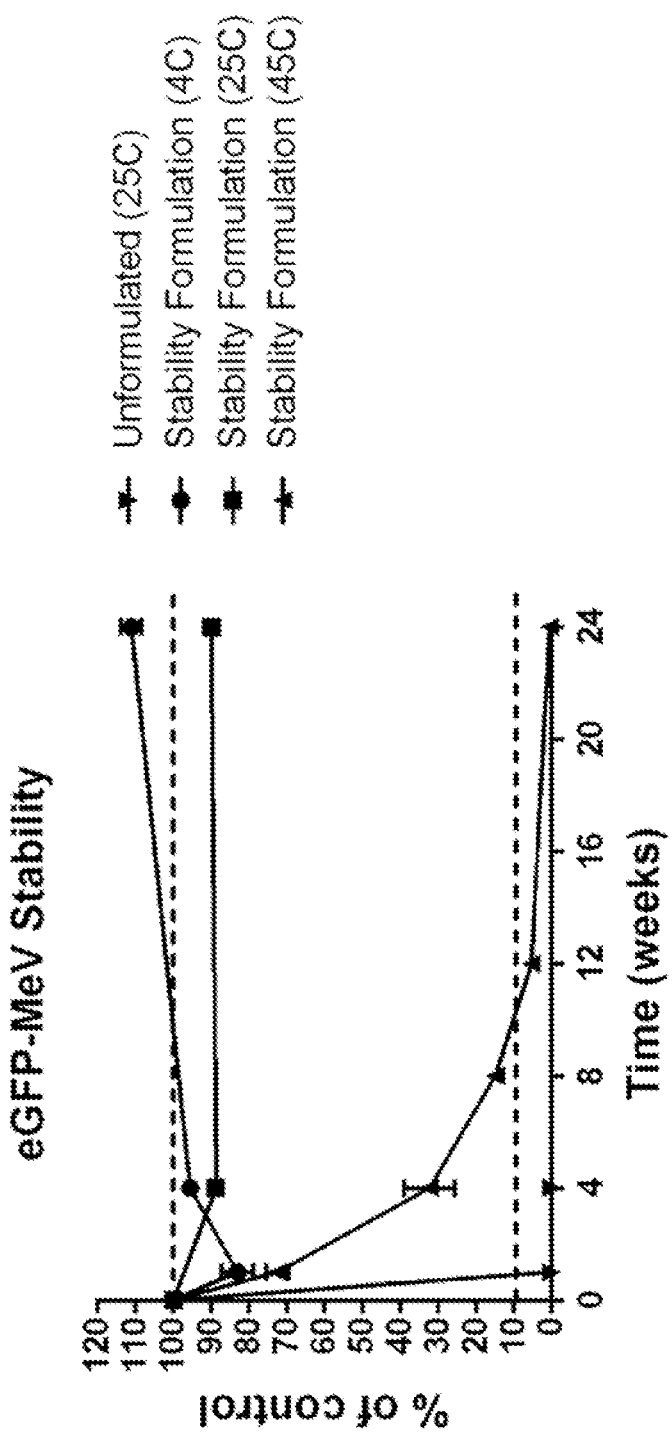
FIG. 12 is a line graph showing the relative eGFP-MeV activity remaining after drying a vaccine formulation including a blend of threonine and sucrose and storage for various periods and temperatures.

The highest performing excipient mixture was then subjected to a longer term experiment to further examine its ability to maintain the infectivity of eGFP-MeV. Samples were stored at a range of temperatures for up to 2 months. After storage for 1 week at room temperature (25° C.), the control sample which did not include any stabilizing excipients had lost 100% of its infectivity as measured using the eGFP assay. Samples which included the stabilizing solution (threonine+sucrose) performed much better (FIG. 12). The samples stored at 4° C. and 25° C. retained on average 95% and 89% of their activity respectively after 1 month of storage. Samples stored at the higher temperature (45° C.) had significantly higher loss at this time point, retaining only 32% of their infectivity as measured using eGFP fluorescence detection. At the final 6 month time point, the samples stored at the lower temperatures proved to be very stable. The 4° C. and 25° C. samples retained 100% and 90% of their original infectivity respectively. The samples stored at 45° C. maintained less than 1% of their infectivity at this time point. The rate of decay for the 45° C. sample as calculated by an exponential best-fit line with an $R^2$=0.9961 was found to be k=−0.216. The rate of decay for the 4° C. and 25° C. samples was not calculated because they had not lost a significant amount of activity by the 6 month time point.

While stabilization of the live-attenuated measles vaccine has been previously studied, drying under ambient temperature and pressure is an alternative that has not been well studied. Many vaccine delivery systems such as the microneedle patch are not well-suited to compounds dried using spray drying, lyophilization or similar methods. Thus, these experiments examined the ability of commercially available, human-approved excipient compounds to stabilize the measles vaccine after drying and subsequent storage. Excipient formulations which contained both a sugar and an amino acid demonstrated far superior stabilizing potential than either excipient showed when tested individually. The most effective formulation included a mixture of threonine and sucrose and was able to maintain nearly complete measles vaccine activity as measured by our eGFP assay after 6 months at 4° C. and 25° C. It was also able to maintain more than 10% activity at 45° C. for more than 8 weeks.

Example 9

A patch containing micron-scale polymeric needles was formulated to encapsulate measles vaccine. The microneedle patches were produced by a two-step process in which stabilized measles vaccine was filled into micromolds, localizing the vaccine toward the microneedle tips. Microneedle matrix material solution was then cast onto the molds to form the remaining part of the microneedles and patch backing.

The microneedle patch contained 100 pyramidal microneedles, each measuring 600 μm tall, 300 μm wide at the base and tapering to a tip radius of less than 3 μm. The microneedles contained the standard dose of live-attenuated measles vaccine encapsulated in each patch.

Figures 13A, 13B, 13C:
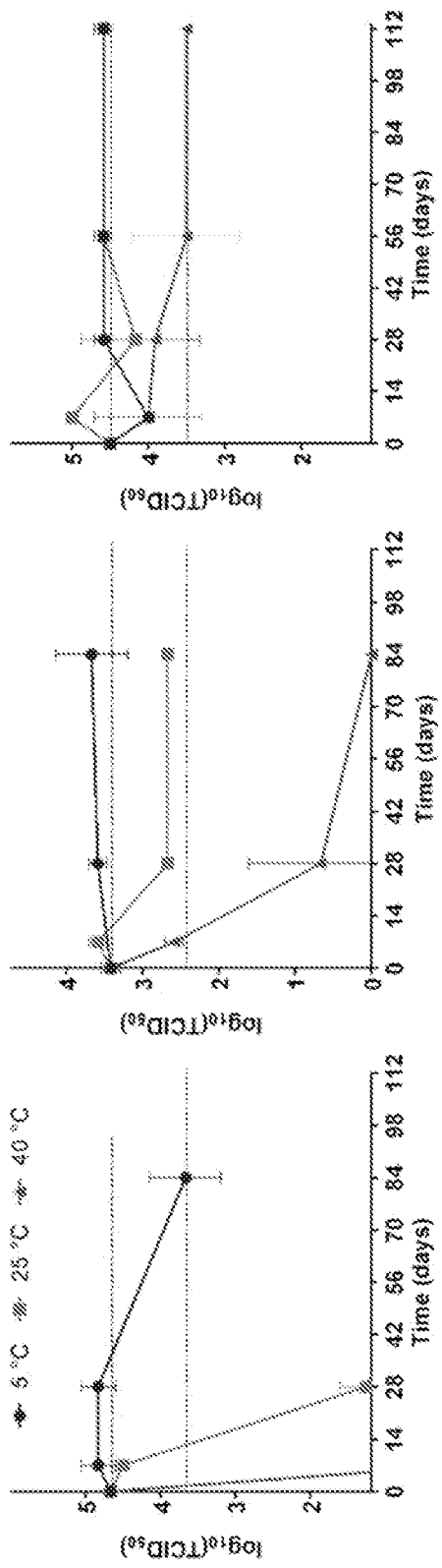
FIGS. 13A-13C shows stability of an exemplary measles vaccine formulation in microneedle patches stored in dessicant pouches (FIG. 13C) as compared to a reconstituted commercial measles vaccine (FIG. 13A) and a commercial lyophilized measles vaccine (FIG. 13B).

The stability of the measles microneedle vaccine was assessed by measuring the vaccine virus titer on microneedle patches stored at various temperatures for almost 4 months. Reconstituted liquid measles vaccine was unstable and lost essentially all potency within 28 days at 25° C. and in less than one week at 40° C. (FIG. 13A-13C). Commercially available lyophilized vaccine also demonstrated instability at 40° C., losing more than 100-fold infectivity after 28 days and more than 1000-fold infectivity within 3 months. In contrast, the microneedle patch maintained full potency for almost four months at 25° C. and lost less than 10-fold infectivity after almost 4 months at 40° C.

A comparison of FIGS. 13A and 13B demonstrates that formulations that are effective at stabilizing the measles vaccine in the solid state are not necessarily effective at stabilizing the measles vaccine in its liquid state. Although the same vaccine formulation was used for the liquid and solid, the stability profiles of the liquid and solid were very different. These observations are more broadly supported by studies which have shown that the stability of vaccine formulations can be significantly reduced when the dry vaccine is reconstituted in liquid.

The unpredictability of whether an excipient will be effective to stabilize a liquid or solid vaccine formulation also is evidenced by differences observed between prior art studies of liquid vaccine stability and the results of the present application. For example, while previous studies identified lactose as stabilizing liquid measles vaccine formulations, lactose was not capable of stabilizing dry measles vaccine formulations. Compare, e.g., Kissmann J, et al., "Stabilization of measles virus for vaccine formulation," Hum. Vaccine 4(5):350-9 (2008), and Example 8. Sucrose, however, was effective at stabilizing both liquid and solid forms of measles vaccine formulations. Id.

Example 10

The immune response following measles vaccination using the microneedle patch of Example 9 was evaluated in rhesus macaques. The rhesus macaque is a well-established model for measles vaccination studies since the immune response in macaques shows a strong correlation to the human immune response. One group of monkeys received a standard human dose of the live-attenuated measles vaccine via a microneedle patch and the positive control group received the same dose of vaccine via subcutaneous injection.

The microneedle patch could be pressed into the skin with a force of 28 N, which corresponds to 0.28 N per microneedle, in good agreement with previous findings. This force can readily be applied by a human thumb. Microneedles dissolved rapidly upon insertion into porcine cadaver skin. Within one minute, the tips of the microneedles dissolved. Within 10 minutes, the microneedles were almost completely dissolved.

To minimize vaccine wastage and provide accurate dosing, it was confirmed that the measles vaccine was concentrated within the microneedles, which enter the skin, rather than in the patch backing. Prior to use, each patch used for vaccination of monkeys contained approximately 3100 $TCID_{50}$ of measles vaccine. Ten minutes after manual application to the skin of rhesus macaques, the microneedle patch backing and any remaining microneedle stubs contained 9.4±2.2% of the original vaccine loaded into the microneedle patches, indicating that more than 90% of the vaccine dose was delivered to the skin.

Serum samples were obtained weekly and tested for antibodies to measles virus. To monitor the progress of the immune response, serum samples were tested for the presence of measles-specific IgM by ELISA. Measles-specific IgM was detected for every animal in both groups as early as day 14 post vaccination. The presence of measles-specific IgM antibodies confirmed that all of the animals had generated a primary immune response to measles following vaccination.

Neutralizing antibodies were first detected beginning 21 days post vaccination and increased to a peak on day 28 of approximately 4700 mIU/mL in both groups. The peak titers and the times to peak titer were not significantly different between the two groups ($p>0.05$). In both the microneedle patch and subcutaneous injection groups, all of the animals seroconverted and all of the animals had a titer of >120 mIU/mL, which is considered protective in humans. Neutralizing antibody titers were maintained for at least 133 days post vaccination. Overall, both vaccines generated a robust antibody response in the rhesus macaques and these data show that measles vaccination using a microneedle patch induced equivalent neutralizing antibody titers to vaccination by conventional subcutaneous injection. The timing and magnitude of the antibody responses were similar to those observed following experimental vaccination of rhesus macaques by subcutaneous injection in prior studies.

The immunogenicity of the microneedle patch was compared with subcutaneous injection in rhesus macaques (*Macaca mulatta*), as approved by the Institutional Animal Care and Use Committees of the CDC and the Georgia Institute of Technology. Measles neutralizing antibody titers were measured by the plaque reduction neutralization assay. Two-fold dilutions of serum were tested starting at a dilution of 1:4. An enzyme-linked immunosorbent IgM assay previously developed at the CDC41 was used to detect serum IgM antibodies to measles virus. Results were determined by using the standard cut-off values.

The microneedle patch did not require reconstitution with diluent, dissolved in skin within 10 minutes, and caused only mild, transient skin erythema. Both groups of rhesus generated neutralizing antibody responses to measles that were consistent with protection and the neutralizing antibody titers were equivalent. In addition, the microneedle patches maintained an acceptable level of potency after storage at elevated temperature suggesting improved thermostability compared to standard lyophilized vaccine. Therefore, a measles microneedle patch vaccine was immunogenic in non-human primates, and this approach offered a promising delivery method that could help improve vaccination coverage.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

The invention claimed is:

1. A vaccine composition comprising:

an influenza antigen, and an excipient selected from the group consisting of maltodextrin 17, maltodextrin 4, arginine, histidine, calcium heptagluconate, maltodextrin 13, heparin, raffinose, arabitol, fructose, potassium gluconate, adonitol, xylitol, sodium thiosulfate, asparigine, 2-hydroxypropyl-β-cyclodextrin, TRIS, sodium citrate, dulcitol, and combinations thereof, wherein the composition is in a dry solid form which is in the form of a dissolvable microneedle or a dissolvable microneedle coating.

2. The vaccine composition of claim 1, wherein the excipient is present in the composition in an amount from about 1% to about 90% by weight.

3. The vaccine composition of claim 1, wherein the influenza antigen is selected from the group consisting of influenza A, influenza B, influenza C, and combinations thereof.

4. The vaccine composition of claim 1, wherein the influenza antigen comprises a whole inactivated influenza virus, a split inactivated influenza virus, a subunit inactivated influenza virus, an influenza virus-like particle, or a combination thereof.

5. The vaccine composition of claim 1, further comprising one or more adjuvants.

6. The vaccine composition of claim 1, wherein the influenza antigen is characterized as having improved stability over six months in the composition as compared to a comparative composition comprising the influenza antigen without an excipient.

7. The vaccine composition of claim 1, wherein the influenza antigen is characterized as having improved stability over three months in the composition as compared to a comparative composition comprising the influenza antigen without an excipient.

8. The vaccine composition of claim 1, wherein the influenza antigen maintains at least 50% of its activity after three months of storage at temperatures up to 40° C.

9. The vaccine composition of claim 1, wherein the influenza antigen maintains at least 75% of its activity after three months of storage at temperatures up to 40° C.

10. A vaccine composition comprising:
an influenza antigen, and
a blend of excipients selected from the group consisting of trehalose and arginine; trehalose and calcium heptagluconate; trehalose and maltodextrin 13; sucrose and arginine; arginine and calcium heptagluconate; arginine and maltodextrin 13; calcium heptagluconate and maltodextrin 13; maltodextrin 13 and sodium citrate; maltodextrin 13 and lactose; and sorbitol and sodium citrate,
wherein the composition is in a dry solid form which is in the form of a dissolvable microneedle or a dissolvable microneedle coating.

11. The vaccine composition of claim 10, wherein the blend of excipients is present in the composition in a total amount from about 1% to about 90% by weight.

12. The vaccine composition of claim 10, wherein the excipients of the blend are present in the composition at a ratio from about 1:15 to about 15:1.

13. The vaccine composition of claim 10, wherein the excipients of the blend are present in the composition at a ratio of about 1:1.

14. The vaccine composition of claim 10, wherein the influenza antigen is selected from the group consisting of influenza A, influenza B, influenza C, and combinations thereof.

15. The vaccine composition of claim 10, wherein the influenza antigen comprises a whole inactivated influenza virus, a split inactivated influenza virus, a subunit inactivated influenza virus, an influenza virus-like particle, or a combination thereof.

16. The vaccine composition of claim 10, further comprising one or more adjuvants.

17. The vaccine composition of claim 10, wherein the influenza antigen is characterized as having improved stability over six months in the composition as compared to a comparative composition comprising the influenza antigen without one or more excipients.

18. The vaccine composition of claim 10, wherein the influenza antigen is characterized as having improved stability over three months in the composition as compared to a comparative composition comprising the influenza antigen without one or more excipients.

19. The vaccine composition of claim 10, wherein the influenza antigen maintains at least 50% of its activity after three months of storage at temperatures up to 40° C.

20. The vaccine composition of claim 10, wherein the influenza antigen maintains at least 75% of its activity after three months of storage at temperatures up to 40° C.

21. A vaccine composition comprising:
an influenza antigen, and
an excipient blend comprising sucrose and arginine,
wherein the composition is in a dry solid form, and is in the form of a dissolvable microneedle or a microneedle coating.

22. A transdermal patch comprising a base and an array of microneedles which extend from the base and comprise the vaccine composition of claim 1.

23. A method of vaccinating a patient comprising:
inserting one or more microneedles across the stratum corneum of the patient's skin, wherein the one or more microneedles comprise the vaccine composition of claim 1,
wherein the vaccine composition dissolves in vivo over a dissolution period from about 1 second to about 1 hour.

24. A vaccine composition comprising:
an influenza antigen,
an excipient selected from the group consisting of maltodextrin 17, maltodextrin 4, arginine, maltose, histidine, calcium heptagluconate, maltodextrin 13, heparin, raffinose, myo-inositol, sucrose, sorbitol, arabitol, fructose, potassium gluconate, adonitol, xylitol, sodium thiosulfate, asparigine, 2-hydroxypropyl-β-cyclodextrin, TRIS, sodium citrate, dulcitol, and combinations thereof, and
a buffer salt comprising HEPES, ammonium acetate, or potassium phosphate dibasic,
wherein the composition is in a dry solid form which is in the form of a dissolvable microneedle or a dissolvable microneedle coating.

25. The vaccine composition of claim 10, wherein the composition further comprises HEPES, ammonium acetate, or potassium phosphate dibasic.

26. The vaccine composition of claim 21, wherein the composition further comprises HEPES, ammonium acetate, or potassium phosphate dibasic.

27. A vaccine composition comprising:
an influenza antigen;
an excipient selected from sucrose, trehalose, arginine, maltodextrin, calcium heptagluconate, and combinations thereof; and
a buffer salt selected from HEPES, ammonium acetate, and potassium phosphate dibasic,
wherein the composition is in a dry solid form which is in the form of a dissolvable microneedle or a dissolvable microneedle coating.

* * * * *